United States Patent [19]

Okada et al.

[11] Patent Number: 5,672,158
[45] Date of Patent: Sep. 30, 1997

[54] CATHETER INTRODUCER

[75] Inventors: Yosuka Okada, Morimachi Ichimyyia; Munehito Kurimoto, Asaba-cho, both of Japan

[73] Assignee: Sherwood Medical Company, St. Louis, Mo.

[21] Appl. No.: 90,098

[22] PCT Filed: Jan. 5, 1993

[86] PCT No.: PCT/US93/00437

§ 371 Date: Jul. 6, 1994

§ 102(e) Date: Jul. 6, 1994

[87] PCT Pub. No.: WO93/13822

PCT Pub. Date: Jul. 22, 1993

[30] Foreign Application Priority Data

Jan. 7, 1992 [JP] Japan .................. 4-000161 U
Jan. 29, 1992 [JP] Japan .................. 4-002826 U

[51] Int. Cl.$^6$ .................................. A61M 5/00
[52] U.S. Cl. .................. 604/164; 604/165; 604/166; 128/772
[58] Field of Search .................. 604/164, 165, 604/166, 169, 170, 171, 280, 281, 282, 283; 128/772

[56] References Cited

U.S. PATENT DOCUMENTS

| | | | |
|---|---|---|---|
| 2,623,520 | 3/1952 | Bamford, Jr. et al. | 128/221 |
| 3,348,544 | 10/1967 | Braun | 604/164 |
| 3,352,306 | 11/1967 | Hirsch | 604/164 |
| 3,406,685 | 10/1968 | May | 128/214.4 |
| 3,454,006 | 7/1969 | Langdon | 604/164 |
| 4,013,080 | 3/1977 | Froning | 128/347 |
| 4,192,305 | 3/1980 | Seberg | 128/214.4 |
| 4,230,123 | 10/1980 | Hawkins, Jr. | 604/165 X |
| 4,233,974 | 11/1980 | Desecki et al. | 128/215 |
| 4,345,606 | 8/1982 | Littleford | 128/784 |
| 4,362,156 | 12/1982 | Feller, Jr. et al. | 604/165 |
| 4,417,886 | 11/1983 | Frankhouser et al. | 604/53 |
| 4,431,426 | 2/1984 | Groshong et al. | 604/280 |
| 4,445,893 | 5/1984 | Bodicky | 604/165 |
| 4,549,879 | 10/1985 | Groshong et al. | 604/247 |
| 4,559,046 | 12/1985 | Groshong et al. | 604/282 |
| 4,609,370 | 9/1986 | Morrison | 604/165 |
| 4,675,007 | 6/1987 | Terry | 604/283 |
| 4,737,152 | 4/1988 | Alchas | 604/256 |
| 4,772,266 | 9/1988 | Groshong | 604/164 |
| 4,790,331 | 12/1988 | Okada et al. | 128/772 |
| 4,798,591 | 1/1989 | Okada | 604/164 |
| 4,813,938 | 3/1989 | Raulerson | 604/167 |
| 4,955,890 | 9/1990 | Yamamoto et al. | 606/108 |
| 4,973,313 | 11/1990 | Katsaros et al. | 604/165 |
| 5,004,456 | 4/1991 | Botterbusch et al. | 604/53 |
| 5,026,351 | 6/1991 | Dizon | 604/164 |
| 5,064,414 | 11/1991 | Revane | 604/165 |
| 5,064,415 | 11/1991 | Walder et al. | 604/171 X |
| 5,098,392 | 3/1992 | Fleischhacker et al. | 604/165 |

(List continued on next page.)

FOREIGN PATENT DOCUMENTS

| | | |
|---|---|---|
| 0008451 | 3/1980 | European Pat. Off. . |
| 0171077 | 2/1986 | European Pat. Off. . |
| 0258566 | 3/1988 | European Pat. Off. . |

*Primary Examiner*—Sam Rimell
*Attorney, Agent, or Firm*—Montgomery W. Smith; Richard D. Allison

[57] ABSTRACT

A catheter introducer (31) which allows a dilator section (33) and a sheath section (32) to be engaged with and disengaged from each other promptly and smoothly. The catheter introducer (31) is composed of a sheath section (32) consisting of a sheath (35) and a sheath hub (34) and a dilator section (33) consisting of a dilator (38) and a dilator hub (36). The dilator hub (36) includes a flange (37) to cover the end of said sheath hub 34) in the state of engagement formed at the distal end of the dilator hub (36), a circular groove (40) formed in the internal circular portion of the flange (37) or in the external circular portion of the sheath hub (34), and a protrusion (39) to be engaged with said groove wherein the protrusion is formed on the external circular portion of the sheath hub or on the internal circular portion of the flange.

15 Claims, 7 Drawing Sheets

U.S. PATENT DOCUMENTS

| | | | |
|---|---|---|---|
| 5,104,381 | 4/1992 | Gresl et al. | 604/164 |
| 5,125,904 | 6/1992 | Lee | 604/164 |
| 5,129,891 | 7/1992 | Young | 604/283 |
| 5,300,106 | 4/1994 | Dahl et al. | 607/119 |
| 5,312,337 | 5/1994 | Flaherty et al. | 604/93 |
| 5,352,205 | 10/1994 | Dales et al. | 604/158 |

1

CATHETER INTRODUCER

TECHNICAL FIELD

The present device relates to a catheter introducer for introducing a catheter into a blood vessel.

BACKGROUND ART

In a device to introduce a catheter into a blood vessel such as for angiography, a catheter introducer is used. As shown in FIG. 1, symbol 1 denotes a catheter introducer in general. The catheter introducer 1 includes a sheath section 2, a dilator section 3, a sheath hub 4, a sheath 5, a female hole 6, a dilator hub 7, a dilator 8, a male prism 9, and a side tube 10.

As can be seen in the drawing, the prior art catheter introducer log FIG. 1 is composed of the sheath section 2 consisting of the sheath 5 and the sheath hub 4 and the dilator section 3 consisting of the dilator 8 and the dilator hub 7. The catheter introducer 1 has the dilator section 3 set in the sheath section 2, and is inserted into a blood vessel over a guide wire.

FIGS. 2 and 3 are illustrations showing how the prior art catheter of FIG. 1 introducer is used. In the drawings, symbol 11 denotes a three-way stop cock, a guide wire is designated by symbol 12, subcutaneous tissue is designated by symbol 13, and symbol 14 designates a blood vessel. When the catheter introducer is used, a hollow needle (not illustrated) with an inner needle inserted through it is introduced into the blood vessel 14, and after removing the inner needle, the guide wire 12 is inserted through the hollow needle. The hollow needle is subsequently removed, to leave only the guide wire 12 in the blood vessel. Then, as shown in FIG. 2, the catheter introducer 1 with the dilator section 3 inserted in it is inserted into the blood vessel 14 with the guide wire 12 operating as a guide, and subsequently, with the sheath 5 of the catheter introducer 1 inserted in the blood vessel 14. As shown in FIG. 3, the dilator section 3 and the guide wire 12 are subsequently removed. Then, a catheter is inserted into the sheath 5 which operates to guide the tip of the catheter into the blood vessel 14 to complete the insertion of the catheter into the blood vessel 14. Subsequently, as required, the three-way stop cock 11 may be actuated to supply a medicine, etc. into the blood vessel through the sheath.

If the catheter introducer 1 with the dilator section 3 inserted therein is inserted into the blood vessel 14 with the guide wire operating as a guide while the sheath section 2 is being held and turned clockwise and counterclockwise, the insertion into the blood vessel 14 can be easily achieved. However, to achieve this, any means for mutually arresting the movement of the dilator section 3 and the sheath section 2 is required to prevent the relative rotation between the dilator section 3 and the sheath section 2 as well as preventing the axial displacement thereof.

To prevent the relative rotation and axial displacement of the dilator section 3 with respect to the sheath section 2, several proposals have been disclosed. The proposals are described below. The device as shown in FIG. 1 is disclosed in Japanese Patent Publication No. 91-37430 has a female polygonal hole 6 formed in the sheath section 2 and a male prism 9 formed in the dilator section 3. The male prism 9 of the dilator section 3 is inserted in the female polygonal hole 6 of the sheath section 2 to prevent the relative rotation between the dilator section 3 and the sheath section 2. Furthermore, the female polygonal hole 6 has a groove 6a formed and the male prism 9 has a rib 9a formed so that when the male prism 9 of the dilator section 3 is inserted in the female polygonal hole 6 of the sheath section, the rib 9a of the male prism 9 is fitted in the groove 6a of the female polygonal hole 6 for preventing the axial displacement of the dilator section 3 and the sheath section 2.

FIG. 4 shows a prior art device disclosed in said Japanese Patent Laid-Open No. 90-289269. The male engaging part 15 of the dilator section 3 and the female engaging part 16 of the sheath section 2 are tapered and hexagonal in section. The tapered engagement can prevent the axial displacement and the relative rotation between the sheath section 2 and the dilator section.

A prior art device shown in FIGS. 5 and 6 is also disclosed in the same Japanese Patent Laid-Open No. 90-28269. FIG. 5 is a front view showing the end of the sheath section 2 with a female taper portion 17 with recesses 18 and FIG. 6 is a side view showing the dilator section 3 with a male taper portion 19 with protrusions 20. The male taper portion 19 of the dilator section is inserted into the female taper portion 17 of the sheath section to prevent the axial displacement by the taper portion 17, and to prevent the relative rotation by the engagement between the protrusions 20 and the recesses 18.

The prior art device shown in FIG. 7 is shown in Japanese Utility Model Laid-Open No. 89-112849. In this case, a spiral protrusion 21 is formed around the end 2a of the sheath section and a recess 22 to be engaged with the protrusion 21 of the sheath section is formed in the end 3a of the dilator section 3 for fastening the dilator section 3 and the sheath section 2 by screwing the sections together.

DISCLOSURE OF INVENTION

As described above, several means for engaging the dilator section with the sheath section have been developed, but they are not perfect. In many of the above described devices, the engagement achieved by the interconnection of the tapered portions is weak and unstable and may cause disengagement during use.

The use of protrusions and recesses shown in FIGS. 5 and 6 overcomes this disadvantage to some extent. However, for reliable engagement between protrusions and recesses, the length of engagement between the elements must be long enough to prevent disengagement therebetween. As a result, as shown in FIG. 8, the depth D from the end of the sheath section to the check valve must be long, and in this situation, it is difficult to insert a guide wire or catheter which may be bent or precurved at the tip into the sheath, since the tip of the catheter deviates from the center of the check valve as shown in FIG. 8.

The device shown in FIG. 7 overcomes this disadvantage, but screwing is required for engaging the dilator section with the sheath section which is a troublesome action.

The present invention has been created to solve the problems of the conventional catheter introducers described above, and an object of the present invention is to provide a catheter introducer which allows the dilator section to be engaged with and disengaged from the sheath section promptly and smoothly.

To achieve the above object, the catheter introducer of the present device has a flange formed at the end of the dilator section. The flange covers the end of the sheath hub in engagement with the dilator section. The dilator section also has a groove formed in the internal circular portion of the sheath hub and a protrusion to be engaged with the groove may be formed on the external circular portion of the sheath hub or the internal circular portion of the flange.

In the catheter introducer composed as described above, when the catheter introducer provided with the dilator section is inserted into the blood vessel, the protrusion formed on the sheath section or the dilator section is engaged with the groove formed on the other of the dilator section or the sheath section to integrate the dilator section and the sheath section. So, even if the catheter introducer is inserted into the blood vessel while the sheath section is being held and turned clockwise and counterclockwise, it does not happen that the dilator section and the sheath section are rotated relatively or displaced axially.

For disengaging the dilator section from the sheath section, both can be disengaged by slightly inclining or canting the dilator hub with respect to the sheath hub while pulling on the dilator hub.

BRIEF DESCRIPTION OF DRAWINGS

FIG. 14 is an enlarged perspective view of another embodiment of the present invention;

BEST MODE FOR CARRYING OUT THE INVENTION

Figure 1:
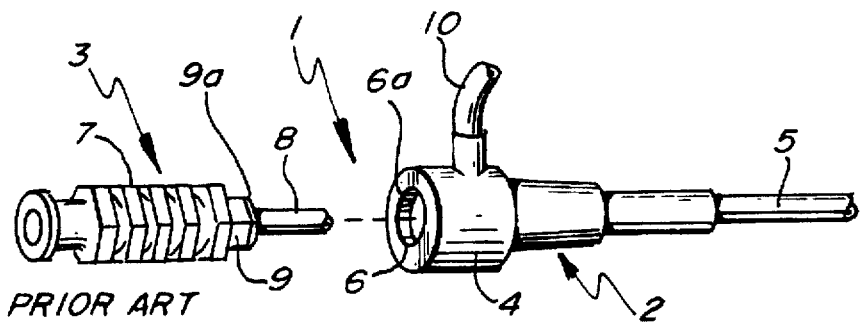
FIG. 1 is a side view showing a prior art catheter introducer.

As can be seen in the drawings, in the catheter introducer of the present invention, the flange 37 with the circular protrusion 39 formed on its internal circular portion is provided at the distal end of the dilator hub 36, and the groove 40 to be engaged with the circular protrusion 39 is formed in the external circular portion of the proximal end of the sheath hub 34 of the sheath section 32. The flange 37 preferably has a plurality of slits 41 thereon formed in the axial direction. It is preferred that the groove 40 is formed to be completely engaged with the circular protrusion 39. It is also possible that the circular protrusion 39 is formed on the external circular portion of the sheath hub 34 of the sheath section 32 while the groove 40 may be formed in the internal circular portion of the flange 37.

Figure 2:
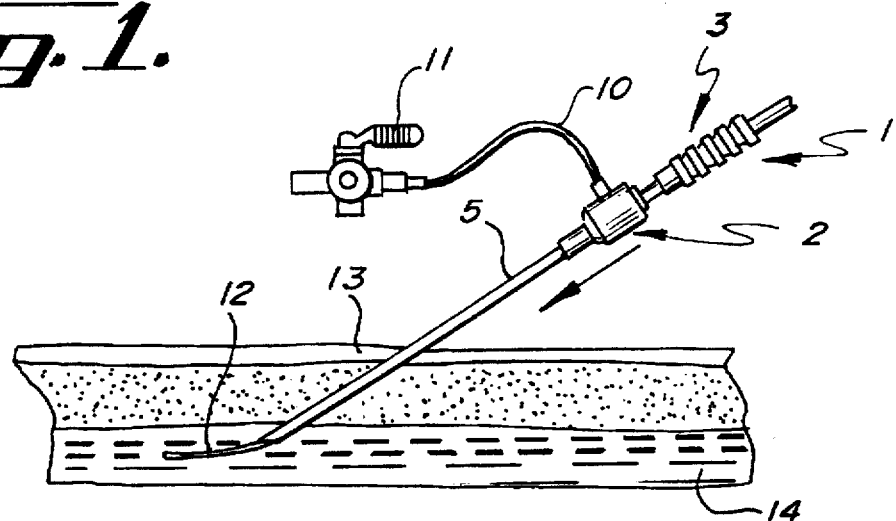
FIG. 2 is a side view of the prior art catheter introducer shown in FIG. 1, showing how the catheter introducer is used.
Figure 3:
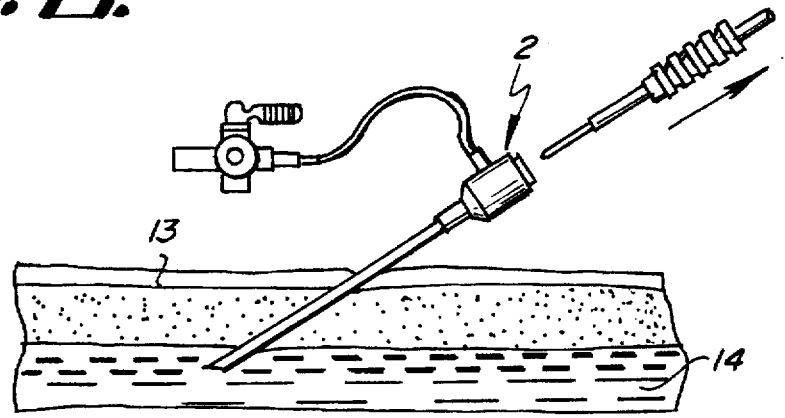
FIG. 3 is a side view of the catheter introducer further showing how the catheter introducer is used.
Figure 4:
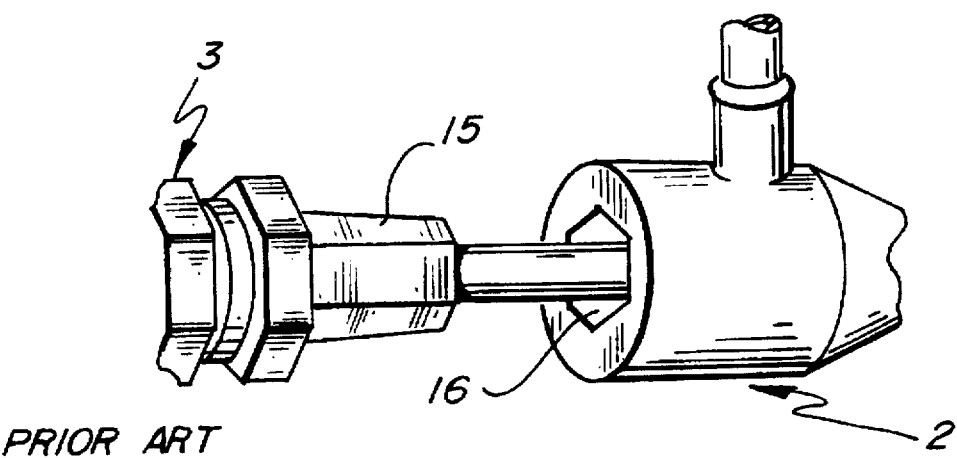
FIG. 4 is a partial perspective view showing a portion of a dilator inserted into a sheath hub of a prior art catheter introducer.
Figure 5:
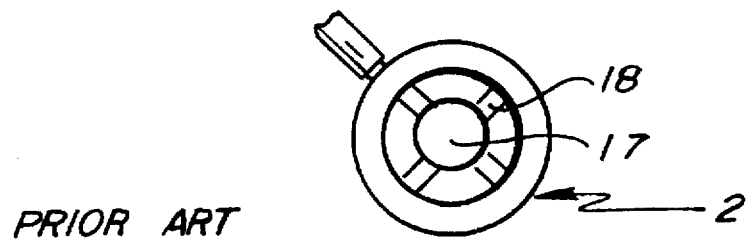
FIG. 5 is a partial front view showing the sheath hub of another prior art catheter introducer.
Figure 6:
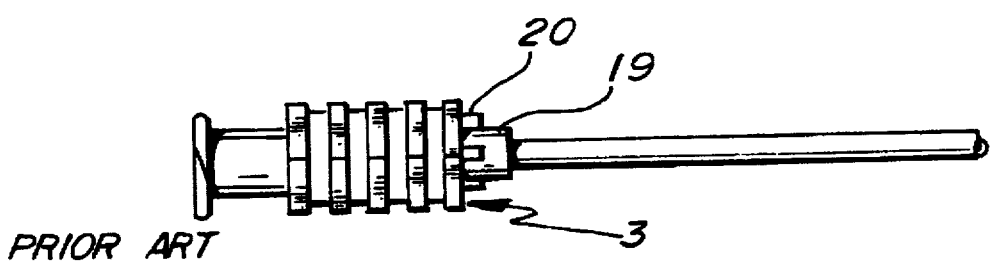
FIG. 6 is a partial side view showing the dilator section of the prior art catheter introducer shown in FIG. 5.
Figure 7:
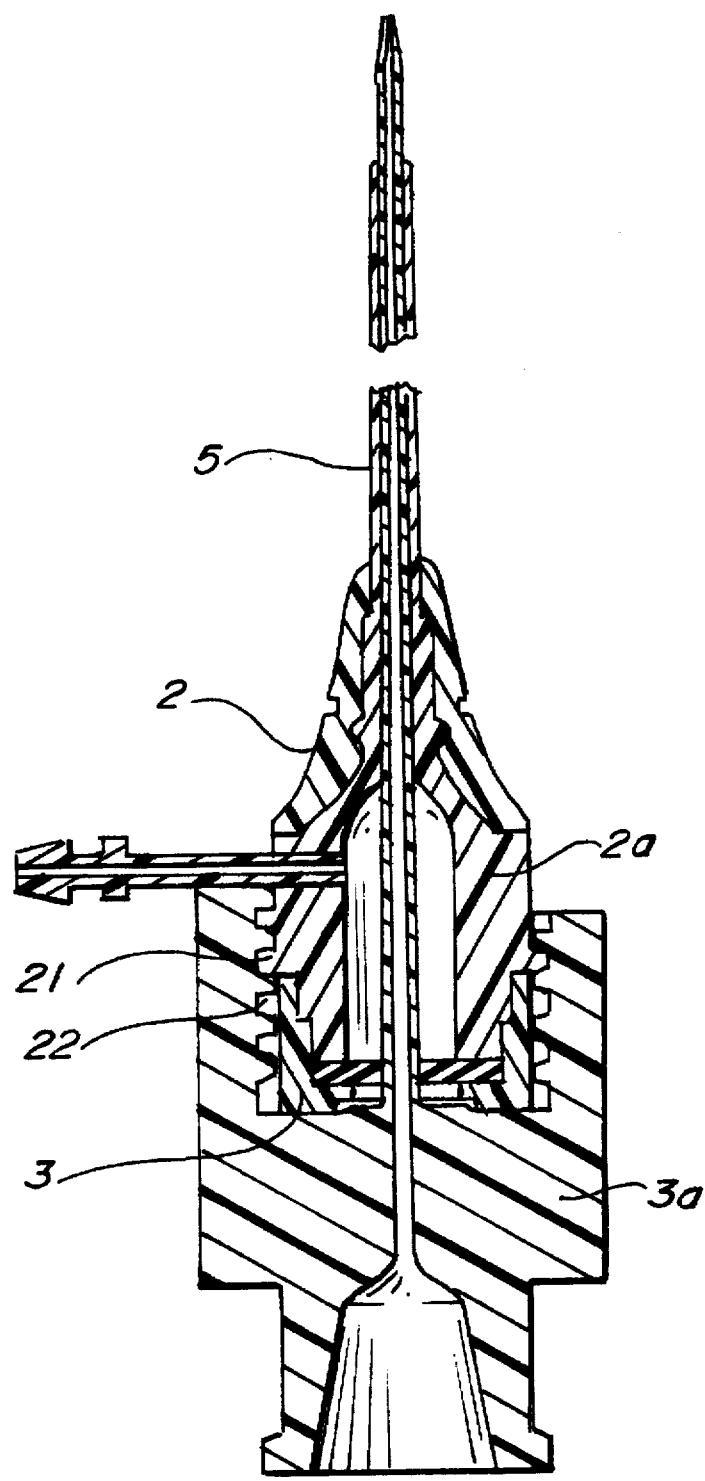
FIG. 7 is a cross-sectional view showing the threaded engagement between the dilator section and a sheath section of a prior art catheter introducer.
Figure 8:
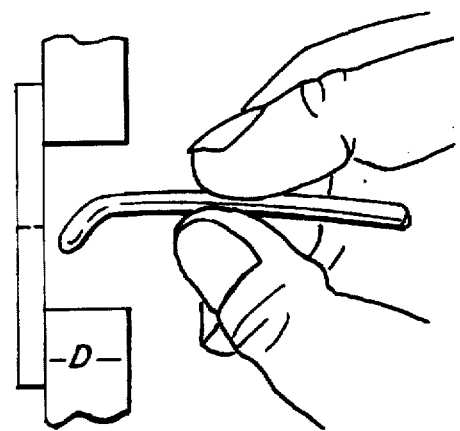
FIG. 8 is an illustration showing where a bent or pre-curved guide wire or catheter is inserted into the sheath of a catheter introducer of the type shown in FIGS. 5 and 6.

When the catheter introducer is inserted into the blood vessel, as illustrated in FIGS. 2 and 3, the dilator 38 of the dilator section 33 is an elongate and tubular member which is inserted into the sheath 35 of the sheath section 32, and the dilator hub 36 is pressed to the sheath hub 34 in the axial direction. Since both the flange 37 and the dilator hub 36 are preferably made of a soft plastic material, the flange 37 covers the external circular portion of the sheath hub 34 in the state of engagement, and the circular protrusion 39 on the flange 37 is engaged with the groove 40 of the sheath hub 34. As a result, the dilator section 33 and the sheath section 32 are integrated, and even if only the sheath section 32 or the dilator section 33 is held and turned clockwise and counterclockwise, it does not happen that the dilator section 33 and the sheath section 32 rotate relatively or are displaced in the axial direction. Therefore, the insertion of the catheter introducer 31 into the blood vessel can be achieved smoothly and easily.

To disengage the dilator section 33 from the sheath section 32, if the proximal end of the dilator hub 36 is lightly pressed or canted in the direction perpendicular to the axial direction, the protrusion 39 of the flange 37 is disengaged from the groove 40 of the sheath 34.

Figure 9:
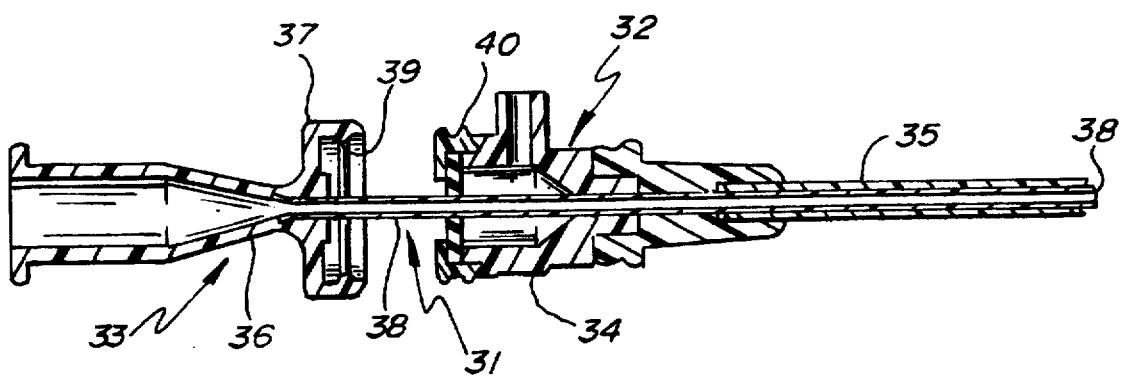
FIG. 9 is an enlarged cross-sectional view showing a catheter introducer as an example of the present invention.
Figure 10:
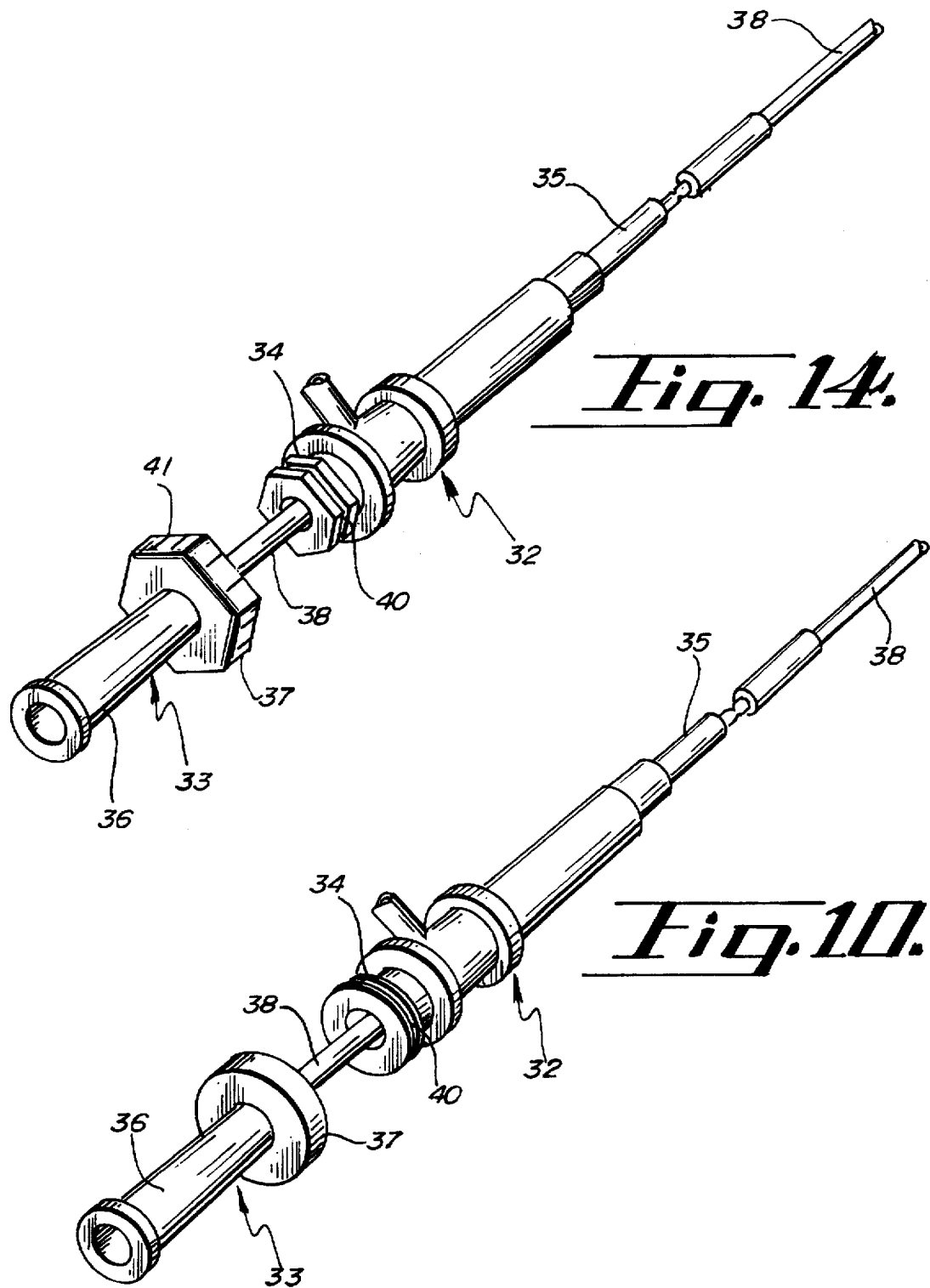
FIG. 10 is an enlarged perspective view showing the catheter introducer of FIG. 9.
Figure 11:
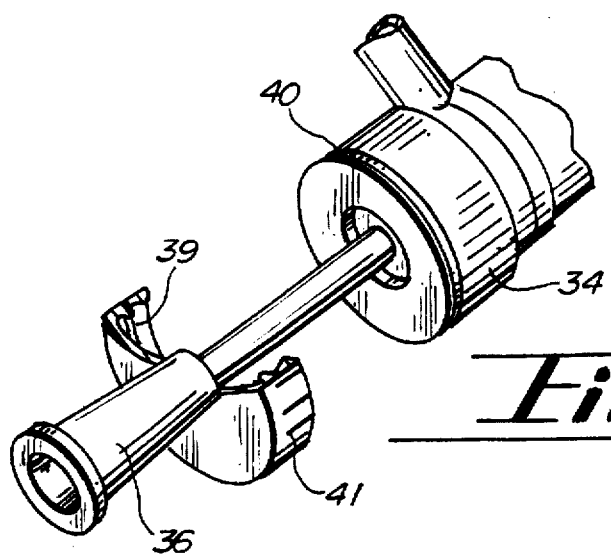
FIG. 11 is an enlarged partial perspective view showing an important portion of a variation of the catheter introducer of FIG. 9.

FIGS. 9-11 are illustrative of a preferred form of the present invention. The catheter introducer is generally referred to herein as catheter introducer 31. The catheter introducer 31 includes a sheath section 32 and a dilator section 33. The sheath section 32 includes a sheath hub 34 having circumferential groove 40 thereon and an elongate sheath 35. The dilator section 33 includes a dilator hub 36 with a flange 37 having a circumferential circular protrusion 39 thereon and an elongate dilator portion 38. Therefore, the insertion of the catheter introducer into the blood vessel can be achieved smoothly and easily.

As shown in FIGS. 9-16 in the catheter introducer 31 of the present invention, a flange 37 is preferably provided around the dilator hub 36 of the dilator section 33 to cover the sheath hub 34 in the state of engagement and a protrusion 39 and a groove 40 to be engaged with each other are formed on or in the flange 37 and the sheath hub 34. So, even if the sheath section 32 of the catheter introducer 31 is held and turned clockwise and counterclockwise for insertion of the catheter into a blood vessel, it does not happen that the dilator section 33 and the sheath section 32 rotate relatively or are displaced in the axial direction and the insertion of the catheter introducer 31 into the blood vessel can be achieved easily and reliably as an excellent effect of the present device.

To disengage the dilator section 33 from the sheath section 32, if the end on the side of the dilator section 33 opposite to the flange 37 of the dilator hub is lightly pressed or canted in the direction perpendicular to the axial direction, the protrusion 39 of the flange is disengaged from the groove 40 of the sheath hub.

Figure 12:
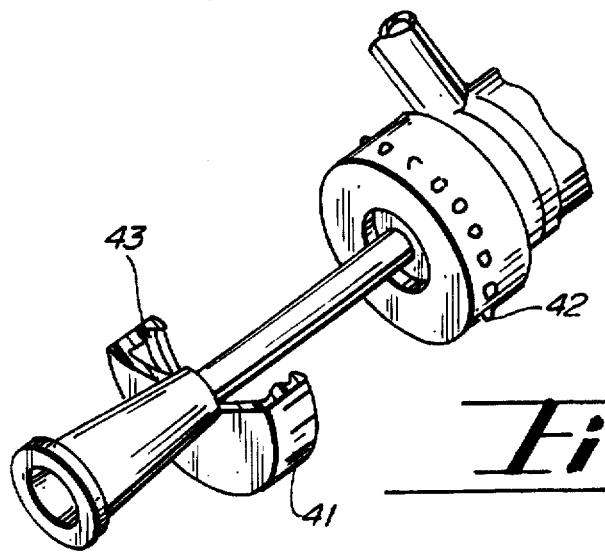
FIG. 12 is an enlarged partial perspective view showing an important portion of another embodiment of a catheter introducer of the present invention.

FIG. 12 is an enlarged partial perspective view showing another example of the present invention. In this embodiment, a plurality of protrusion dots 42 are formed on the external circular portion of the sheath hub 34, and the groove 43 is formed in the internal circular portion of the flange 37 to be engaged with the protrusion dots 42.

Figure 13:
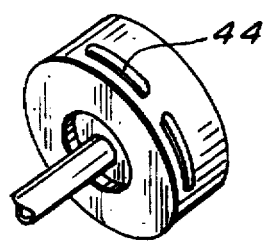
FIG. 13 is an enlarged perspective view showing an important portion of another embodiment of a sheath hub of a catheter introducer of the present invention.

FIG. 13 shows an embodiment of the present invention where protrusion strips 44 are formed along the circumference of the sheath hub 34 instead of the protrusion dots 42 of the above embodiment. In these embodiments, slits 41 are formed in the flange 37.

Figure 15:
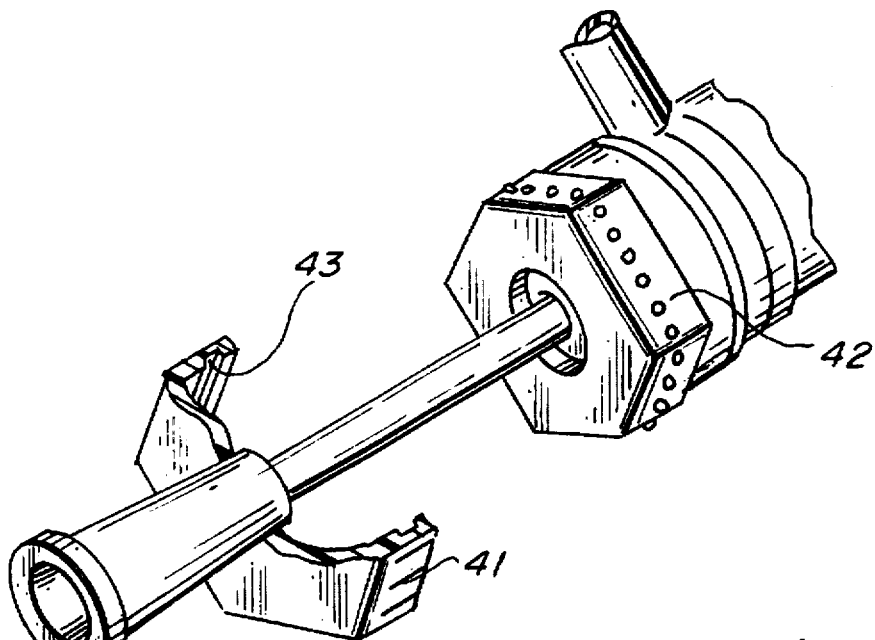
FIG. 15 is an enlarged partial perspective view of an alternate embodiment of the present invention showing the dilator and sheath hubs.
Figure 16:
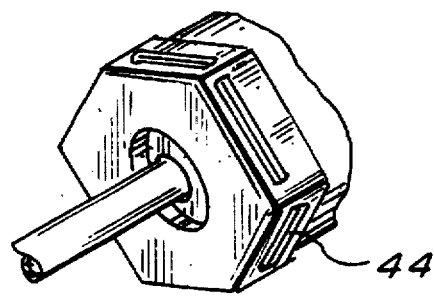
FIG. 16 is an enlarged partial perspective view of the sheath hub of an alternate embodiment of the present invention.

As can be seen in FIGS. 14–16, in the catheter introducer 31 of the present embodiment, a regularly hexagonal flange 37 with the continuous protrusion 39 on the internal circular portion is provided at the end of the dilator section 33 and the sheath hub 34 of the sheath section 32 is formed to be regularly hexagonal with the groove 40 in its external circular portion to allow the hexagonal sheath hub 34 to be fitted in the internal circular portion of the flange 37 at the end of the dilator section. If the sheath hub is fitted in the internal circular portion of the flange 37 at the end of the dilator section 33, the protrusion 39 on the internal circular portion of the flange is fitted in the groove 40 of the sheath hub 34 to prevent the axial displacement of the dilator section 33 and the sheath section 32. Furthermore, since the sheath hub 34 is fitted in the hexagonal internal circular portion of the flange 37, the relative rotation between the dilator section 33 and the sheath section 32 does not occur. Moreover, plural slits 41 are formed in the external circular portion of the flange 37 in the axial direction conveniently for covering the sheath hub 34 with the flange 37 in the state of engagement.

FIG. 15 is an enlarged perspective view showing another embodiment of the present invention. In this embodiment, multiple protrusion dots 42 are formed on the external circular portion of the sheath hub 34 and the groove 43 is formed in the internal circular portion of the flange 37 to be engaged with the protrusion dots 42.

FIG. 16 shows an embodiment where protrusion strips 44 are formed instead of the protrusion dots 42 disclosed in the above embodiment. In these embodiments described above, slits 41 are preferably formed in the flange 37.

With this embodiment, it is also possible to form the protrusion 39 on the external circular portion of the sheath hub 34 of the sheath section and to form the groove 40 in the internal circular portion of the flange 37.

In these embodiments, the internal circular portion of the flange 37 and the sheath hub 32 are formed to be regularly hexagonal but the form is not limited to hexagon. It is only preferred to be a regular polygon which includes a square or pentagon.

When the catheter introducer 31 of the present invention is inserted into the blood vessel in the manner shown in FIGS. 2 and 3, the dilator 38 of the dilator section 33 is inserted into the sheath 35 of the sheath section 31, and the dilator hub 36 is pressed to the sheath hub 34 in the axial direction. Since both the flange 37 and the dilator hub 36 are made of a soft plastic material, the flange 37 covers the external circular portion of the sheath hub 34 in the state of engagement, and the protrusion 39 is engaged with the groove 40 of the sheath hub. As a result, the dilator section 33 and the sheath section 32 are integrated and even if only the sheath section or the dilator section is held and turned clockwise and counterclockwise, it does not happen that the dilator section 33 and the sheath section 32 rotate relatively or are displaced in the axial direction.

We claim:
1. A catheter introducer comprising:
 a sheath section having distal and proximal end portions.
 a generally cylindrical sheath hub formed on said proximal end portion of said sheath section, said sheath hub including an outer circumference and a longitudinal passageway extending therethrough;
 a generally elongate and tubular sheath member formed on said distal end portion of said sheath section, a longitudinal passageway extending therethrough and said passageway extending in flow communication with said passageway of said sheath hub;
 a dilator member having distal and proximal end portions thereof and said dilator member being operatively associated with said sheath member in use;
 a generally cylindrical dilator hub formed on said end portion of said dilator member, said dilator hub including a flange means extending from a distal portion thereof and said flange being sized to receive at least a portion of said sheath hub therewith; and
 means for locking said sheath hub on said dilator hub wherein said means for locking includes at least one protrusion and at least one channel and one of said at least one protrusion and at least one channel is formed on said outer circumference of said sheath hub and the other of said at least one protrusion and at least one channel is formed on said flange member, said at least one protrusion and said at least one channel being formed to interlock such that rotational and longitudinal movement of said sheath hub and said dilator hub is prevented when said at least one protrusion and said at least one channel are interlocked and said at least one protrusion and said at least one channel are sized and oriented to unlock when a lateral force is applied to said dilator hub with respect to said sheath hub to release said sheath hub from said dilator hub.

2. The catheter introducer of claim 1 wherein said flange member includes an inner surface thereon and said inner surface includes said other of said at least one protrusion or|and said at least one channel thereon.

3. The catheter introducer of claim 2 wherein said inner surface of said flange member includes a channel therein and said outer circumference of said sheath hub includes a protrusion thereon.

4. The catheter introducer of claim 3 wherein said protrusion extends along the entire circumference of said outer circumference of said sheath hub.

5. The catheter introducer of claim 3 wherein said flange member is sized to substantially extend along said outer circumference of said sheath hub and said flange includes a plurality of elongate slits therein.

6. The catheter introducer of claim 1 wherein said outer circumference of said sheath hub is formed as a regular polygon and said flange member is formed to include an interior surface having a regular polygonal surface which is complementary to said outer circumference of said sheath hub.

7. The catheter introducer of claim 1 wherein said outer circumference of said sheath hub includes said at least one channel thereon and said flange member includes said at least one protrusion thereon.

8. The catheter introducer of claim 7 wherein said flange member includes an inner surface thereon and said at least one protrusion extends substantially therealong.

9. The catheter introducer of claim 8 wherein said at least one protrusion is formed of a plurality of.

10. The catheter introducer of claim 7 wherein said at least one channel extends along the entire circumference of said outer circumference of said sheath hub.

11. The catheter introducer of claim 7 wherein said flange member includes a plurality of slits thereon.

12. A method of using a catheter introducer, including the steps of;

inserting a dilator member having a dilator hub and dilator thereon into a sheath member having a sheath hub and a sheath thereon such that a flange member on the dilator hub lockingly engages a portion of the sheath hub to prevent rotational and longitudinal movement therebetween;

inserting a portion of the catheter introducer into the body of a patient by rotational and longitudinal movement of the catheter introducer; and applying a generally lateral force to the dilator member with respect to the sheath hub to release the flange member of the dilator member from the sheath hub of the sheath member to allow longitudinal movement between the dilator hub of the dilator member and the sheath hub of the sheath member.

13. The method of claim 12 wherein the application of a generally lateral force to the dilator hub releases a protrusion on the flange member from a channel on the sheath hub.

14. The method of claim 12 wherein the application of a generally lateral force to the dilator hub releases a channel on the flange member from a protrusion on the sheath hub.

15. The method of claim 12 wherein the application of a generally lateral force to the dilator hub expands one or more slits on the flange member.

* * * * *